(12) United States Patent
Kuhn (10) Patent No.: US 7,179,087 B2
(45) Date of Patent: Feb. 20, 2007

(54) MEDICAL OR DENTAL-MEDICAL HANDPIECE HAVING A REARWARD AND A FORWARD HANDPIECE SECTION

(75) Inventor: Bernhard Kuhn, Biberach (DE)

(73) Assignee: Kaltenbach & Voigt GmbH & Co. KG, Biberach (DE)

( * ) Notice: Subject to any disclaimer, the term of this patent is extended or adjusted under 35 U.S.C. 154(b) by 468 days.

(21) Appl. No.: 10/610,903

(22) Filed: Jul. 1, 2003

(65) Prior Publication Data

US 2004/0014000 A1  Jan. 22, 2004

(30) Foreign Application Priority Data

Jul. 2, 2002  (DE) .............................. 102 29 650

(51) Int. Cl.
*A61C 1/08* (2006.01)
(52) U.S. Cl. ...................................... 433/126; 433/114
(58) Field of Classification Search ................ 433/126, 433/114, 130, 131, 133
See application file for complete search history.

(56) References Cited

U.S. PATENT DOCUMENTS

| | | | | |
|---|---|---|---|---|
| 3,909,946 A | * | 10/1975 | Watanabe | 433/126 |
| 4,211,009 A | | 7/1980 | Leonard | 433/126 |
| 4,255,143 A | * | 3/1981 | Schuss et al. | 433/126 |
| 4,278,429 A | | 7/1981 | Straihammer et al. | 433/126 |
| 4,403,959 A | * | 9/1983 | Hatakeyama | 433/126 |
| 4,643,675 A | | 2/1987 | Kuhn | 433/126 |
| 4,647,081 A | * | 3/1987 | Landgraf et al. | 285/304 |
| 4,792,304 A | * | 12/1988 | Schuss et al. | 433/126 |
| 5,020,994 A | * | 6/1991 | Huang | 433/126 |
| 5,230,624 A | | 7/1993 | Wolf et al. | 433/82 |
| 5,252,067 A | * | 10/1993 | Kakimoto | 433/129 |
| 6,106,287 A | | 8/2000 | Yates | 433/82 |

FOREIGN PATENT DOCUMENTS

| | | |
|---|---|---|
| DE | 28 02 325 | 8/1978 |
| DE | 28 55 720 | 7/1980 |
| DE | 34 33 877 | 4/1986 |

\* cited by examiner

*Primary Examiner*—Ralph A. Lewis
(74) *Attorney, Agent, or Firm*—Marshall, Gerstein & Borun LLP (57) ABSTRACT

The invention relates to a medical or dental-medical treatment which at its rearward end has a coupling element for coupling on to a matching coupling element of a flexible supply line, and in its forward region has a holder device for a tool, the handpiece being of a rearward and a forward handpiece section which are connected with one another by means of a plug-in connection and are fixed on one another by means of a latching device which has a latching arm extending approximately axis-parallel and which is transversely elastically bendable, which latching arm is arranged on the one plug-in connection part and is latched in its free end region with a latching element arranged on the other plug-in connection part . For the purpose of improving the connection between the rearward and the forward handpiece section the latching device at the same time axially fixes an insert part of the handpiece, which insert part sits in a plug-in recess of the one and/or of the other plug-in connection part.

14 Claims, 3 Drawing Sheets

Fig. 8

MEDICAL OR DENTAL-MEDICAL HANDPIECE HAVING A REARWARD AND A FORWARD HANDPIECE SECTION

BACKGROUND OF THE INVENTION

1. Field of the Invention

The invention relates to a medical or dental-medical handpiece.

2. Description of Related Technology

A handpiece is described for example in DE 28 02 325 C2. In the case of this known handpiece, having an elongate grip part or shaft in the form of a so-called angled piece, the handpiece consists of a rearward handpiece section and a forward handpiece section which with regard to the rearward handpiece section is arranged at an angle. The handpiece sections are connected with one another by means of a plug-in coupling having a plug-in pin projecting from the rearward handpiece section and a plug-in recess opening out at the rearward end of the forward handpiece section and receiving the plug-in pin, and are axially fixed to one another by means of a latching device. The plug-in pin has a plug-in pin base on which a ring sleeve is fixedly placed, from which there project two rigid latching arms lying diametrically opposite one another, which in their free end regions have in each case on their inside a latching calotte. The forward handpiece section is pushed, with its plug-in recess, onto the ring sleeve and it has in the base region of the plug-in recess two spring arms, arranged diametrically opposite one another, extending rearwardly, having latching noses which are latched into the calotte recesses. An inner sleeve extends coaxially through the plug-in coupling, in which sleeve a drive shaft section is rotatably mounted, and which is pressed into the sleeve-shaped plug-in pin base and is thus axially fixed to the plug-in base.

There is described in DE 34 33 877 C1 a handpiece having an angle-shaped grip part the forward, angled grip part limb of which consists of a rearward and a forward handpiece section, of which the rearward handpiece section has a plug-in recess open to the fore, into which the forward handpiece section can be inserted with a rearwardly projecting plug-in pin and can be axially locked by means of a locking device. The locking device has a latching ball arranged in the wall of the plug-in recess, which through a turning of a rotary sleeve rotatably mounted on the rearward handpiece section is urged into a latch recess in the plug-in pin and through this axially fixes the plug-in pin and thus also the entire forward handpiece section. For release, the rotary sleeve is to be rotated against the force of a return spring in the other circumferential direction, through which the latch ball is released and the forward handpiece section with the plug-in pin can be drawn out of the rearward handpiece section.

SUMMARY OF THE INVENTION

The object of the invention is to improve a handpiece of the kind indicated in the introduction with regard to the connection between the rearward and the forward handpiece section. This improvement is to relate not only to the connection between the handpiece sections, but also to a sleeve-shaped insert part which passes through the rearward and/or forward handpiece section.

In the case of the handpiece in accordance with the invention the latching device serves not only to connect the rearward handpiece section and the forward handpiece section with one another, but also to axially fix an insert part of the handpiece which is inserted into a matching plug-in recess of the rearward and/or forward handpiece section, so that for the axial fixing of the insert part no further fixing device is needed. In particular there is needed no press fitting for the axial fixing of the insert part as is the case with the state of the art. For the connection of the insert part with the forward handpiece section there can likewise be arranged a matching plug-in recess in the forward handpiece section, into which the insert part is or can be placed with its forward end, so that the forward handpiece section sits on the insert part. The axial fixing of the forward handpiece section is thereby ensured by means of the latching device, which connects the forward with the rearward handpiece section. The forward handpiece section is preferably formed by means of the head of the handpiece, from which a plug-in connection part extends rearwardly and is connected with a plug-in connection part of the rearward handpiece section.

The insert part is preferably an insert sleeve through which a drive shaft extends and is mounted by means of rotary bearings in the forward and rearward region of the insert sleeve, in particular by means of roller bearings, the outer rings of which sit in matching end bearing bores of the insert sleeve. The fittings of the plug-in recesses for the insert part have a slight play for movement, so that the insert part is readily insertable and mountable in the plug-in recesses. Through this there is provided a simple structure and simple mounting or de-mounting, which can also be economically manufactured and quickly mounted or de-mounted.

For a functional latching it is sufficient if a latching device having a latching element is arranged on one side or eccentrically neighbouring the insert sleeve. Preferably, two latching devices, each with a latching element, are arranged to both sides of the insert sleeve, whereby the at least one latching element fulfils the latching function both between the rearward and forward handpiece section and also between the rearward and/or the forward handpiece section and the insert sleeve. It is advantageous for further reasons of simplicity and stability if the latching between the rearward handpiece section or the forward handpiece section and the insert part remains effective, i.e. does not release during a de-latching between the rearward and the forward handpiece section, but retains its latching. Through this the mechanical connection of the insert part is maintained.

In the case of a handpiece of the kind concerned, there is required a cross-sectional size which is as small as possible, in particular in the forward region of its shaft, in order to affect as little as possible the view of the treatment site even at restricted treatment or operation sites. This applies in particular for a dental-medical handpiece, since the mouth of the patient is a restricted treatment site, the accessability to which through the mouth opening is additionally made more difficult. On the other hand, the cross-sectional size of the forward end region of the shaft must not be so small that stability problems arise, in particular when there is involved a handpiece in which a drive shaft is rotatably mounted.

In one embodiment, the end piece is configured so that a small cross-sectional size for the forward region of the handpiece can be realised.

With the configuration in accordance with one embodiment of the invention, the latching arm of the latching device is arranged with its rearward end on the rearward handpiece section and it extends from the rear forwardly.

This configuration in accordance with the invention is based on the insight that the radial structural size of the at least one latching arm can be reduced in the direction to the fore, without the necessary stability of the latching arm being affected. This is due to the fact that the latching arm must be most stable in its base region and with increasing distance forwardly from the base region can be formed less stably, because due to the forwardly decreasing lever arm in the case of a radial loading the torque effective on the latching arm reduces with increasing spacing from the base region. This forwardly reducible structural size benefits the cross-sectional size of the handpiece because this forwardly reduced cross-sectional size of the spring arm benefits the per se known forwardly reduced cross-sectional size of the handpiece and thus the cross-sectional size can be reduced overall. This configuration is of benefit in particular for a dental-medical handpiece, because due to the restricted working area in the mouth region of a patient any reduction of constructional size, no matter how small, is of significance, in particular in the forward region of the handpiece, which is the case due to the natural restriction of the mouth opening.

A further objective of the invention is to provide an end piece with an exceptionally small radial structure.

With a handpiece of the kind under consideration there arises the risk that contaminants in the medium to be delivered, in particular water, which are scarcely to be avoided, can affect or block the media line in particular in the forward region of the handpiece, e.g. in the region of the outlet nozzle. In order avoid or reduce this risk it has already been proposed to form a handpiece with a lateral plug-in recess in the region of the media line whereby through the plug-in opening a cartridge of a cleaning device can be mounted and de-mounted in the plug-in recess. In the case of such a configuration, however, there is needed a closure of the plug-in opening, which makes the structure more complex. Further, through the presence of the closure, the appearance of the handpiece is worsened.

A further object of the invention is to improve a handpiece while ensuring a simple structure with regard to the mounting or de-mounting of a cartridge.

With the configuration in accordance with a further embodiment of the invention the plug-in recess for the cartridge is arranged in the rearward end region of the handpiece and is accessible from the rear side of the handpiece. Since the rear side of the handpiece is covered by the associated connection part, it is not visible and thus neither it nor a specific closure part spoil the appearance of the handpiece. Since the closure part can be omitted, the structure is also substantilly simplified and economical.

This configuration in accordance with the invention is suited not only for cleaning devices but also for cartridges of other kinds, which are connected by means of a delivery line with an outlet opening in the handpiece directed at the treatment site.

In the case of a cleaning device for a media line, in particular for water, this configuration in accordance with the invention is particularly suitable if the handpiece is connectable with a rearward connection part by means of a so-called plug-in/turn coupling, whereby the media line passes through the plug-in/turn coupling in a Z-shape. With this configuration, the transversely or radially directed section of the media line can be connected in a simple manner with the plug-in recess for the cartridge, so that the media line passes through the plug-in recess in an angled form and the rearward region of the cartridge needs no throughflow, and therefore a simple construction is attained. The rearward region of the cartridge can serve as a stopper for the sealing and mounting of the cartridge, preferably by means of a threading.

The invention also relates to a cartridge as an insert part, for which the above-indicated arguments and advantageous likewise apply.

Further developments of this configuration in accordance with the invention make possible a large throughflow cross-section in the region of the cartridge and also small and economically producible configurations, which in other respects ensure a reliable functioning.

The invention also relates to the cartridge as a individual part, to which the above-described advantages likewise apply.

BRIEF DESCRIPTION OF THE DRAWINGS

Below, advantageous configurations of the invention will be described in more detail with reference to preferred exemplary embodiments and associated drawings. There is shown.

DETAILED DESCRIPTION

Figure 1:
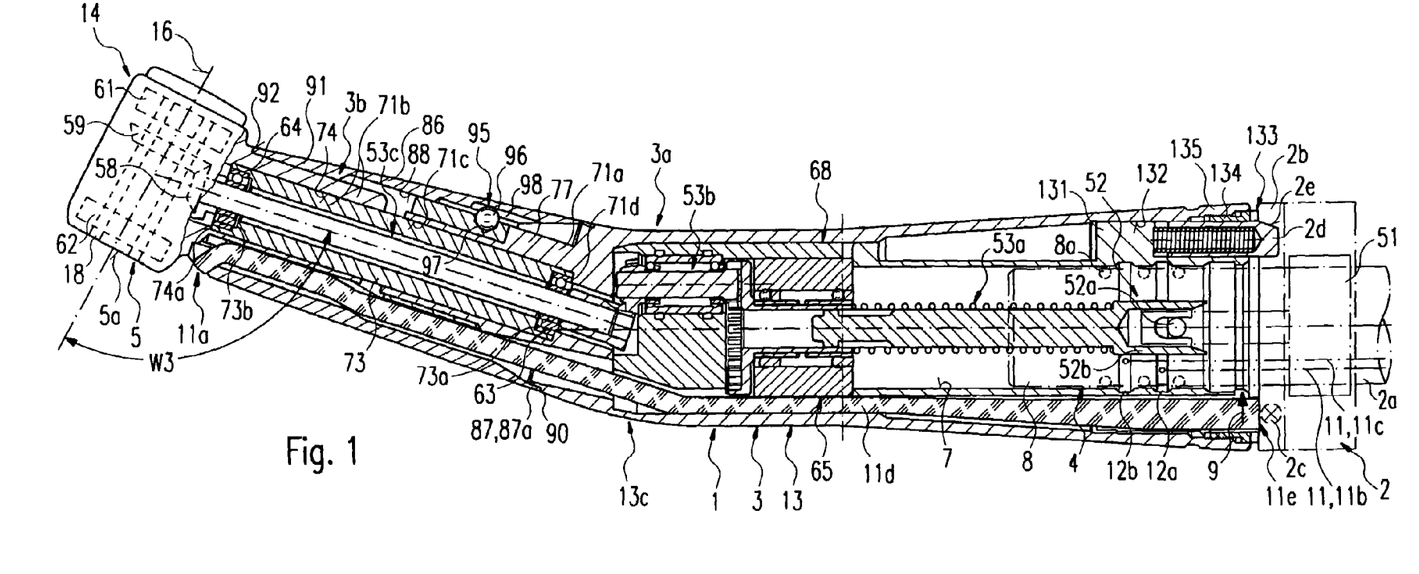
FIG. 1 a treatment instrument in accordance with the invention having a handpiece and a connection part, in a side view, partly axially sectioned.
Figure 2:
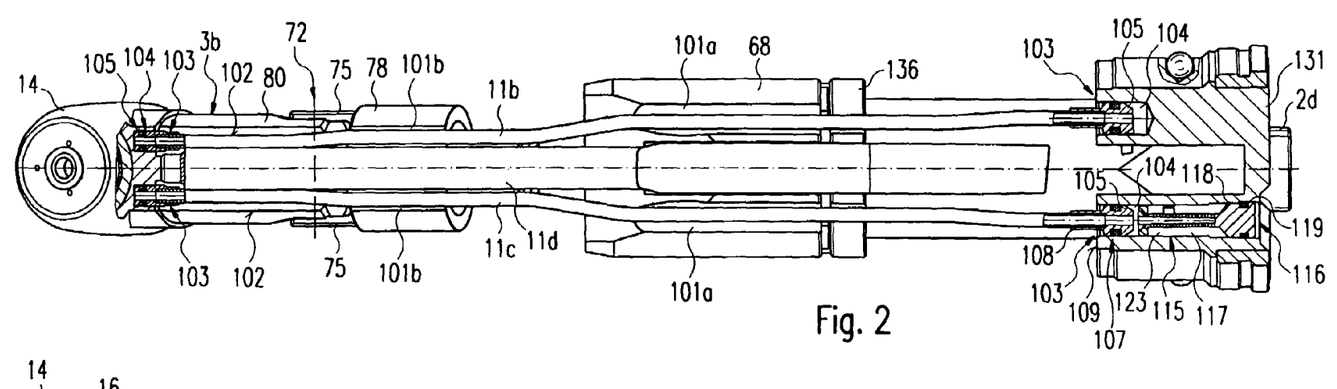
FIG. 2 the handpiece, in a view from below, in a pre-mounted condition.

The treatment instrument, designated overall by 1 in FIG. 1, is of a rearward instrument part, namely a so-called connection part 2, and forward instrument part, namely a so-called handpiece 3, which are releasably connected with one another by means of a coupling 4, in particular a plug-in coupling, preferably a plug-in/turn coupling. With the present exemplary embodiment there is arranged at the forward end of the treatment instrument 1 a holder device 5 having a forward or—not illustrated—lateral plug-in opening 5a for a non-illustrated tool, whereby the tool can project to the side or forwardly. The handpiece 3 may extends straight (not illustrated) or curved or angled towards the side away from the plug-in opening 5a. The plug-in/turn coupling is formed by means of a coupling recess 7, round in cross-section, and a coupling pin 8 which can be inserted therein with slight play for movement. In the case of the present exemplary embodiment, the coupling recess 7 is arranged at the rearward end of the handpiece 3, and the substantially cylindrical coupling pin 8 extends from the connection part 2 forwardly. In the coupled condition, the coupling recess 7 and the coupling pin 8 are releasably latched with one another by means of a latching device 9. This has a latching element which is radially movably mounted in the one coupling part and biassed by means of a spring force into a latching position passing through the dividing joint, in which position the latching element engages into a ring groove in the other coupling part. Such a latching device 9 latches self-actingly upon coupling, and upon de-coupling it can be overcome by means of manual exercise of an axial pulling force, whereby the latching element is self-actingly displaced into its release position.

The connection part 2 is connected with a flexible supply line 2a, which is connected with a non-illustrated control apparatus. The handpiece 3 is preferably freely rotatably mounted on the coupling pin 8, whereby handling is improved. Through the plug-in/turn coupling 4 there extends at least one media line 11 for a treatment or drive medium, e.g. water, compressed air or a water/air mixture (spray). The media line 11 can extend axially through a radial dividing joint (not illustrated), or Z-shaped through a hollow cylindrical dividing joint between the coupling recess 7 and the coupling pin 8, whereby the media line 11 passes through the dividing joint in the region of a ring groove 12a or 12b in the coupling pin 8 or in the coupling recess 7, so that in any rotary position the passage of media is ensured. To both sides of the passage, the dividing joint is sealed off by means of a sealing ring 8a, which may be arranged in a ring groove in the wall of the coupling recess 7 or in the outer surface of the coupling pin 8. Through this, a free rotatability through $360_E$ and more is ensured. The media line 11 extends from the rearward end of the treatment instrument 1 to its forward end region, whereby it may run in part as a channel in the instrument body or as a tube or pipe line. The media line 11 opens out in the forward end region of the treatment instrument 1, out of this, whereby the mouth opening 11a is directed at the treatment site or at the tip of the tool.

In the case of the present exemplary embodiment there are provided two media lines 11b, 11c for compressed air and water or a water/air mixture (spray) which extend to the two sides of a light conductor lid. The light conductor 11d extends approximately axis-parallel on or in the wall of the handpiece 3 surrounding the coupling pin 8, whereby its rearward end forms a light entry opening 11e at the rearward end face of the handpiece 3. The forward end of the light conductor ends in the region of the mouth opening 11a of the media lines 11b, 11c, preferably between the mouth openings 11a. On the connection part 2 on the forward side, here on the coupling pin 8, a rotary ring 2b is rotatably mounted in which a lamp 2c is arranged in a position before the entry opening 11e, which lamp is connected by means of slip ring contacts with a current circuit (not shown) extending through the supply line 2a. Appropriate positioning of the lamp 2c is ensured by means of a cam connection between the handpiece 3 and the rotary ring 2b. An associated cam 2d is arranged, with reference to the light conductor lid, offset in circumferential direction on the handpiece 3, preferably displaceable between a projecting position and a position retracted into a receiving hole of the handpiece 3, and biassed by means of a spring into the projecting position, so that upon coupling and rotation of the handpiece 3 it can self-actingly latch into a latch recess 2e of the rotary ring 2b.

The handpiece 1 thus has a shaft 13 which may be configured in one piece or may be of a rearward and a forward handpiece section 3a, 3b, which are releasably connected with one another at the start of the arc or in the region of the apex 13c of the angle or in the region of the forward handpiece section 3b. At the forward end of the shaft 13 there is located a thickened head 14 in which a receiving sleeve 18 is rotatably mounted, into the plug-in opening 5a of which the tool can be inserted with its shaft and is releasably fixable by means of a fixing device in per se known manner.

With this treatment instrument 1 a drive 51, e.g. an electric motor, is arranged in the connection part 2 illustrated by chain lines and is drivingly connected with the receiving sleeve 18 by means of a drive shaft or a drive shaft chain 53 having at least two drive shaft sections connected with one another in the apex region in a compression proof manner. In the region of the plug-in coupling 4, the drive shaft train 53 has a plug-in coupling 52 having two plug-in coupling elements 52a, 52b corresponding to one another in a form-fitting manner, through which upon coupling and de-coupling of the plug-in coupling 4 at the same time a coupling and de-coupling of the plug-in coupling 52 is possible.

A drive shaft section 52a arranged in the rearward handpiece section 3a of the handpiece 3 extends up into the beginning region of the curvature or into the apex region of the angled shaft 13, whereby its forward end may be drivingly connected with a third drive shaft section 53c by means of a second drive shaft section 53b extending, for example axially, substantially only in the curvature or development or in the apex region, which third drive shaft section extends in the forward handpiece section 3b up to the receiving sleeve 18 and is drivingly connected with this. The drive shaft section 53a is connected through the plug-in coupling 52 with the motor shaft of the drive motor 51. For the connection of the drive shaft sections 53a, 53b, 53c there is provided in each case a gear transmission.

The drive connection between the third drive shaft section 53c and the receiving sleeve 18 is formed by means of an angled gear transmission having a conical gear 58 on the forward end of the third drive shaft section 53c and a conical gear 59 on the receiving sleeve 18. The gear teeth engagement between the conical gears 58 and 59 is, with regard to the third drive shaft section 53c, arranged on its side away from the plug-in opening 5a. Through this, the drive sleeve 18 is driven in the same rotary direction as the first drive shaft section 53a. The receiving sleeve 18 is rotatably mounted in the head 14 by means of two roller bearings 61, 62, which bearings have a spacing from one another directed along the axis of rotation 16 which is greater than the conical gear 58, so that the latter can be arranged therebetween, including the conical gear 59, which is arranged on the side of the conical gear 58 away from the plug-in opening 5a and at the same time is arranged on the side of the roller bearing 61 towards the plug-in opening 5a, so that the plug-in opening 5a is arranged further distant than the other roller bearing 62. For the rotatable mounting of the third drive shaft section 53c there is arranged in each case a roller bearing 63, 64 on the end regions of this drive shaft section 53c, the outer rings of which sit and are mounted in each case in a matching longitudinal hole of the handpiece section 3b.

The configuration of the gear as a hollow gear makes possible, with a radially small structure, a relatively great step up of the speed of rotation between the first and the second drive shaft section 53a, 53b.

The angle W3 enclosed in FIG. 1 between the middle axis of the forward handpiece section 3b and the axis of rotation 16 of the receiving sleeve 18 is more than $90_E$, preferably substantially $100_E$. Such a configuration is, taking into account the anatomy of the mouth of a patient, particularly favourable.

The forward and the rearward handpiece section 3a, 3b are releasably connected with one another by means of a plug-in connection 71 having a plug-in pin 71a and a plug-in hole 71c, receiving the plug-in pin with a small play for movement, and a latching device 72 for mutual latching in the plugged together position. In the exemplary embodiment, the plug-in pin 71a extends rearwardly from the forward handpiece section 3b, and the plug-in recess 71c opens out forwardly at the forward end of the rearward handpiece section 3a, whereby both plug-in connection parts are preferably formed to be cylindrical or hollow cylindrical and the plug-in pin 71a fits in the plug-in recess 71c with slight play for movement. The plug-in pin 71a is formed by means of a preferably hollow cylindrical bearing sleeve 73 which sits with slight play for movement in a sleeve hole 74 of the corresponding size and shape in the forward handpiece section 3b, whereby it may also be fixedly pressed into the sleeve hole 74. The forward or third drive shaft section 53c extends through the bearing sleeve 73 with play for movement. Preferably, the two bearings 63, 64 of the drive shaft section 53c are received and mounted in bearing recesses in the end regions of the bearing sleeve 73. This applies in the case of a present exemplary embodiment for the outer rings of the roller bearings 63, 64, which sit in end step recesses 73a, 73b of the bearing sleeve 73. If the bearings are formed by means of sliding bearings they may be each formed by means of a bearing ring which sits in the associated bearing recess 73a, 73b and in which the drive shaft 53c is rotatably mounted with slight play for movement.

In the case of the exemplary embodiment, the plug-in recess 71c is formed by means of a forwardly directed hole widening at the step surface 71d on which the rearward end of the bearing sleeve 73 and the outer ring of the roller bearing 63 bear and through this are or can be rearwardly axially restricted. In the direction forwardly the bearing ring or outer ring of the roller bearing 63 may be restricted by means of the shoulder surface of the rearward bearing recess 73a. In similar manner at the forward end of the bearing sleeve 73 this and/or the bearing ring or the outer ring of the roller bearing 64 can also be restricted at a step surface 74a of the sleeve receiving hole 74 and/or of the bearing recess 73b. For axially fixing the drive shaft section 53c at the bearing rings or inner rings of the roller bearings 63, 64 there may serve the gears or conical gears fixedly placed on the drive shaft section 53c, as can be understood from FIG. 1.

The latching device 72 has at least one latching arm 75 extending approximately axis-parallel from the one plug-in connection part of the plug-in connection 71, which arm is elastically outwardly bendable transversely of the longitudinal axis of the shaft section and is latched in its free end region with a latching element 76 which is arranged on the other plug-in connection part. In the case of the exemplary embodiment, the latching element 75 extends forwardly from the plug-in connection part associated with the rearward handpiece section 3a, here from a forward sleeve attachment 77, which projects from the rearward handpiece section 3a. Thereby, the latching element 75 may stand up from a base ring 78 which sits on the associated plug-in connection part, here on the rearward sleeve attachment 77, preferably in an end-side step-shaped ring recess 79, on the step surface of which the base ring 78 can bear and through this is restricted in the one axial direction. For fixing the base ring 78 this may be fixably connected, e.g. glued, with the plug-in connection part carrying it, or the base ring 78 can be fixedly arranged on the plug-in connection part with a press fit. In the case of the exemplary embodiment, the thickness of the latching arm 75 is, with regard to thickness of the base ring 78, at least outwardly tapered, preferably tapered on both sides, here inwardly tapered in a step-shape.

The latching element 76 can be formed by means of a latching projection which stands radially outwardly from the other plug-in connection part and which the latching arm 75 engages over and behind. For this purpose there may be arranged in the forward end region of the latching arm 75 a latching nose, which stands up radially inwardly from the latching arm 75. In the case of the exemplary embodiment, the latching nose is formed by means of a latching recess 81 in the inner side of the latching arm 75, with which the latching arm 75 elastically snaps onto the latching projection and engages behind this.

It is particularly advantageous to form the latching projection by means of an additional pin-like component 82 in particular a ball, which sits in a preferably round and radially through-going receiving hole 83 in the other plug-in connection part, and the radial dimension of which is so great that it projects beyond the inner surface of the sleeve hole 74 radially inwardly and engages into a recess 84 in the outer surface of the bearing sleeve 73. Through this the bearing sleeve 73 is form-fittingly connected with the forward sleeve attachment 80 of the forward handpiece section 3b and fixed both in the circumferential direction and also in the axial direction. The recess 84 is preferably formed by means of a cone-like depression, whereby the round component 82, preferably formed by means of a ball, bears on the cone surface of the depression and in the base of the depression has free space.

It is also advantageous for the latching recess 81 to form it by means of a cone-like depression, so that the round component 82, preferably formed by means of a ball, also bears on the cone surfaces of this depression. Due to the relatively slight thickness of the flat latching arm 75, this depression can run out at the outside of the latching arm 75.

The formation of the latching arm 75 on the base ring 78 has the advantage that these parts can be manufactured in one piece of elastically bendable metal, in particular spring steel, and the carrier of the base ring 78, here the sleeve attachment 77, need not be manufactured of elastic metal or spring steel.

Figure 3:
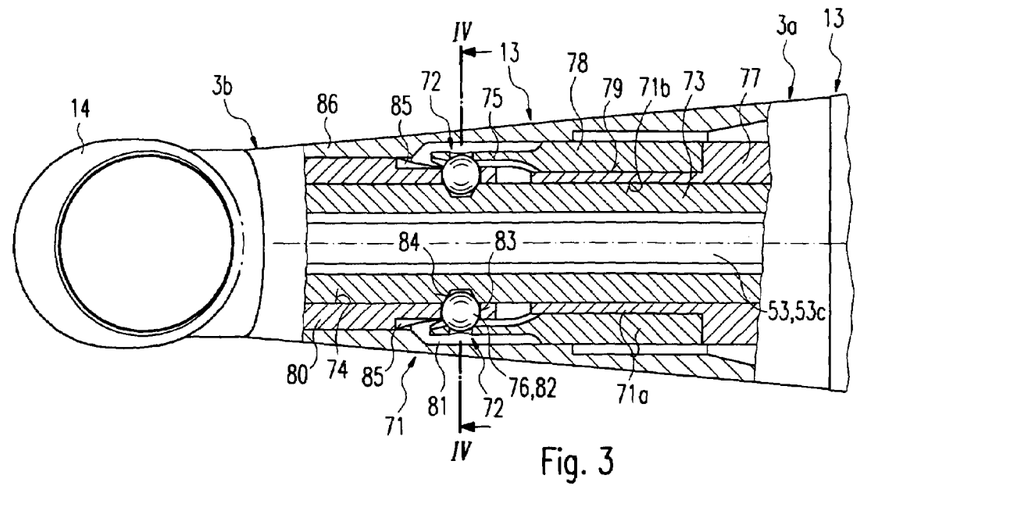
FIG. 3 a forward region of the handpiece, in a partly sectioned view from above.

As can be understood particularly clearly from FIG. 3, the configuration of the latching arm 75 extending forwardly from the sleeve attachment 77 makes possible a small structural size in the transverse direction of the forward handpiece section 3b, which is determined through the external tapering of the latching arm 75 with regard to its carrier, here the base ring 78 or the sleeve attachment 77. Preferably it is thereby determined that the latching arm can be arranged radially inwardly offset so that the also the external contour of the forward handpiece section 3b can be formed with a correspondingly slight cross-sectional size. Here it is to taken into account that in the region of the treatment site, in this case in the mouth of a patient, little space is available and thus any cross-section reduction is of great significance.

A further cross-sectional reduction can be obtained in that the latching arm 75 engages into an external recess 85, e.g. a flattening, of the sleeve attachment 80.

Figure 4:
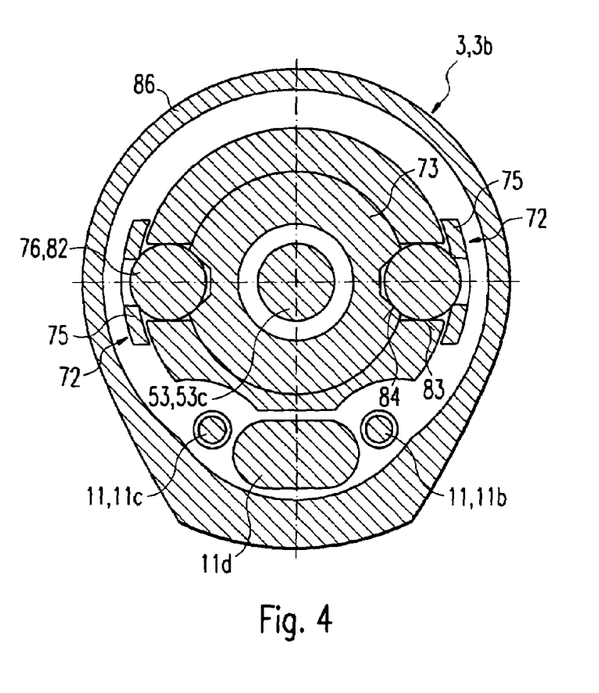
FIG. 4 the section III—III in FIG. 3.
Figure 5:
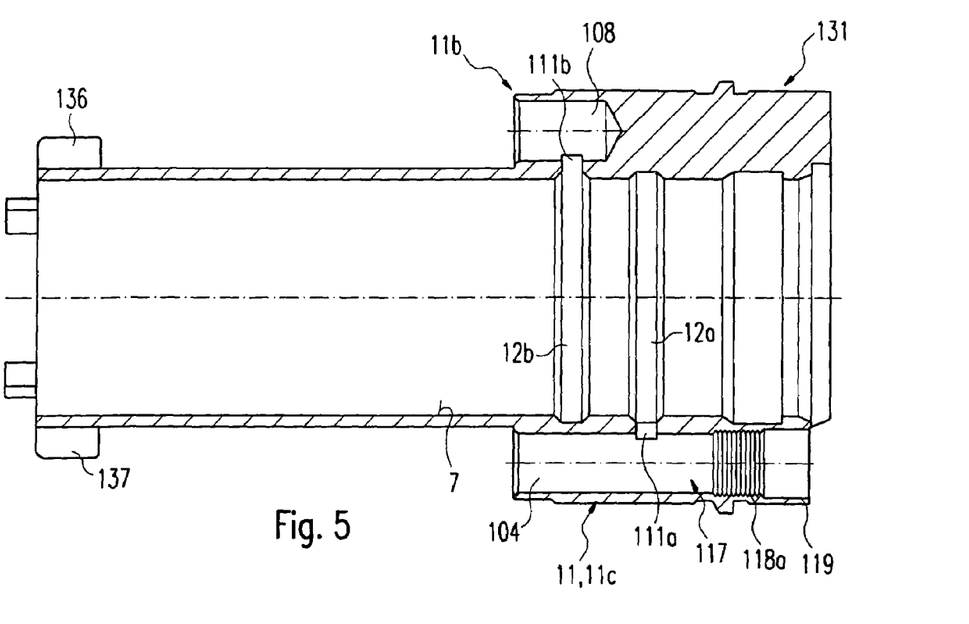
FIG. 5 an insert sleeve, coaxially placed in the rearward end of the handpiece, in an illustration to an enlarged scale and as individual part.
Figure 6:
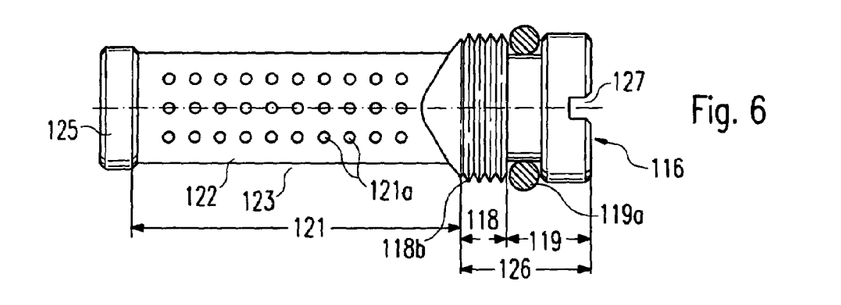
FIG. 6 a cleaning insert in a side view, to an enlarged scale, which can be placed into a receiving hole of the insert sleeve, axis-parallel from the rear.
Figure 7:
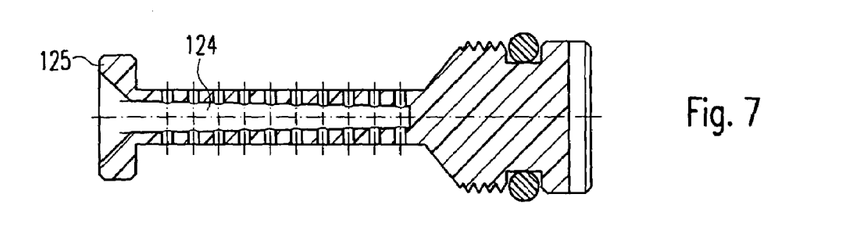
FIG. 7 the cleaning insert according to FIG. 6, in axial section.
Figure 8:
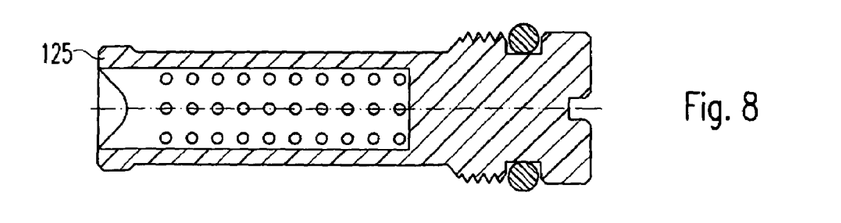
FIG. 8 the cleaning insert according to FIG. 6, in a view from above and in axial section.

As can be understood in particular from FIG. 4, in the absence of recesses 85 a further reduction of cross-section is attained in that the latching arm 75, formed in cross-section by means of a flat strip, is curved corresponding to the curvature of the circumference of the sleeve attachment 80 which is present, or is correspondingly angled in a ridged roof shape.

With the exemplary embodiment there are arranged two latching devices 72 diametrically opposite one another in a mirror image form, through which the latching forces can be doubled and moreover symmetrical latching forces are provided.

A latching procedure and a release of the latching can be carried out readily and rapidly. For latching, the plug-in connection parts 71a, 71b are plugged together in a position in which the latching arm or arms 75 axially coincide with the position of the associated latching projection. Locating this rotary position can be facilitated when in each case a recess 85 is associated with the latching arm 75 and the forward end of the latching arm 75 is rounded in the radial direction of view, or the corners of the latching arm 75 are chamfered. Here, the rounding or the chamfering acts as lead-in surfaces which lead and position the latching arm 75 into the correct circumferential position in the recess 85.

Further, in the case of the exemplary embodiment, the sleeve attachments 77, 80 are, with reference to the configuration of the handpiece sections 3*a*, 3*b* located therebehind and therebefore, tapered over the entire circumference and surrounded by an external sleeve 86 which at its rearward and its forward end ends approximately flush with the configuration of the remaining rearward handpiece section 3*a* and forward handpiece section 3*b*. The outer sleeve 86 has in its rearward region at least one, preferably two, namely a rearward and a middle, sleeve sections, 87, 88 with which the outer sleeve section or sections sit on one or two matching pin sections with slight play for movement. The rearward sleeve section 87 is formed by means of an internal cross-sectional widening at the rearward end of the outer sleeve 86, which is of such size that a tapered ring wall remains in the region of the sleeve section 87. This outwardly tapered sleeve section sits in a step-like ring groove 87*a* with a step surface 90 on the rearward handpiece section 3*a*.

The second middle sleeve section 88 is formed by means of a bore section in the middle region of the outer sleeve 86, into which the forward end of the sleeve attachment 77 engages with slight play for movement.

On the forward end of the outer sleeve 86 this has a sleeve section 91 and an inner cross-section which sits on the sleeve attachment 80 with slight play for movement, which is tapered with regard to the forward region of the forward handpiece section 3*b*, forming a step surface 92. The length dimensions of the outer sleeve 86, the sleeve attachments 87, 80 and the sleeve sections 87, 88, 91 are so formed that in the assembled condition of the plug connection 71 the forward and rearward edge of the outer sleeve 86 bears on the step surfaces 90, 92 through which the inner space surrounded by the outer sleeve is covered over sealingly.

The outer sleeve 86 is positioned against being turned by means of a rotation blocking device 95. The rotation blocking device may be arranged between the outer sleeve 86 and the rearward handpiece section piece 3*a* or the forward handpiece section 3*b*, in particular the sleeve attachments 77, 80. In the exemplary embodiment, the rotation blocking device 95 is arranged between the outer sleeve 86 and the sleeve attachment 77 or the base ring 78, whereby in the mounted condition it is arranged protected under the outer sleeve 86. It can be formed by means of a blocking pin 96, which engages into matching recesses 97, 98 in the outer surface of the sleeve attachment 77 and in the inner surface of the outer sleeve 86, whereby one of the recesses runs out, counter to the insertion direction, on the associated component in the form of a groove, through which axial installation of the outer sleeve 86 is possible.

With the exemplary embodiment, the blocking pin 96 is formed by means of a ball, whereby the recess 97 is formed by means of a calotte and the recess 98 in the outer sleeve 86 is formed by means of a longitudinally developing groove which runs out rearwardly, so that the outer sleeve 86 can be pushed onto the sleeve attachment 77 from the fore, or the rearward handpiece section 3*a* can be pushed into the outer sleeve 86 pushed on to the sleeve section 80, whereby the latching is effected at the same time and self-actingly.

For release, the handpiece sections 3*a*, 3*b* are pulled apart from one another with a manual pulling force, whereby the latching arm 75 self-actingly springs out and releases.

For a release of the connection device at the place of treatment, e.g. by the dentist, the latching force is so dimensioned that the at least one latching device 72 can be overcome by means of manual pushing together or pulling apart of the connection parts, and is thus latchable or delatchable. If, in contrast, a release at the place of treatment, e.g. in a practice, is not to be possible e.g. for reasons of safety, the latching force is so much greater that a connection or release can only be carried out with the aid of tools, in particular in a workshop.

The media lines 11*b*, 11*c* and the light conductor 11*d* extend in the region between the rearward end of the rearward handpiece section 3*a* and the forward handpiece section 3*b* in a through-going manner, whereby they run in associated grooves 101*a*, 101*b*, 102 in the carrier body 86 and/or base ring 78 and/or in the sleeve attachment 80, and may be formed by small tubes, which are connected and sealed in each case by means of a plug-in connection 103 with the rearward end region the handpiece 3 or the forward handpiece section 3*b*. The plug-in connections 103 are in each case formed by means of a preferably cylindrical plug-in recess 104 in the handpiece 3 and a plug-in pin 105 which can be inserted sealingly therein, which pin is sealingly connected with the associated media line 11*b*, 11*c*, has an axial through-channel and is sealed by means of a ring seal 107 in the plug-in recess 104, which is formed by means of a sealing ring, which sits in an outer ring groove in the plug-in pin 105 or in an inner ring groove in the plug-in recess 104 and in each case seals the abutting inner surface of the plug-in recess or the outer surface of the plug-in pin 105. For connection with the media line 11*b*, 11*c* a connection sleeve 108 may extend from the plug-in pin 105, onto or into which sleeve the media line 11*b*, 11*c* is pushed and sealed, e.g. by means of a sealing medium such as a glue or by means of a press fit. For the installation of these line connections it is merely necessary to connect the plug-in pin 105 with the media line and plug it into the plug-in recess 104, or vice versa. In particular in the region of the rearward end of the media lines 11*b*, 11*c* it is advantageous to let the plug-in recesses 104 open out forwardly in each case at an end surface section 109 running transversely, in particular approximately at right angles, to the middle axis of the rearward handpiece section 3*a*, so that the media lines extending approximately axis-parallel can be installed or arranged without bending. The plug-in recesses 104 are in each case connected by means of a transverse channel 111*a*, 111*b* with an associated ring groove 12*a*, 12*b*, which have an axial spacing from one another. In this manner, in functional operation of the hand instrument 1, the Z-shaped throughflow of the medium or media through the hollow cylindrical dividing joint of the plug-in/turn coupling 4 is ensured.

In order to protect contaminants, held in the medium or media in the form of small particles, from a flow transport to the associated outlet opening 11*a* or nozzle, there is arranged in the rearward region of the handpiece in the at least one media line 11, here in the water line 11*c*, a cleaning device 115 which is formed by means of the plug-in recess 104, which is extended with regard to the associated plug-in 105, and a cleaning cartridge 116, which is releasably sealingly inserted or insertable into the extended region of the plug-in recess 104 from the side away from the associated plug-in pin 105, here from the rear into the plug-in recess 104.

Since the connection of the hose or of the small tube of the associated media line 11, 11*c* can be also be constituted other than in the manner of a plug-in connection 103, e.g. with a screw-in connection piece, in the following the extended region of the plug-in recess 104 into which the cartridge 116 can be placed is designated by the reference sign 117. For the axial fixing of the cartridge 116 in the plug-in recess 117 there is provided in the case of the exemplary embodiment a threaded connection 118, having an inner thread 118*a* in a widened wall section of the plug-in recess 117 and an outer thread 118*b* on the cartridge 116. The threaded connection 118 is preferably arranged in the rearward region of the cartridge 116 or of the plug-in recess 117, whereby the threaded connection 118 is preferably arranged before a rearward sealing section 119. In the region of the sealing section 119 there is provided a sealing ring 119*a* which is preferably arranged in the middle region of the sealing section 119 and sits in a ring groove which is arranged in the cylindrical surface of the sealing section 119 of the cartridge 116 or in the hollow cylindrical inner surface of the sealing section 119 of the plug-in recess 117.

As shown in particular in FIGS. 5 to 8, the cartridge 116 has a longitudinally extending cleaning section 121 which is greater in size than the cross-sectional size of the cartridge 116 and through which the medium to be cleaned flows transversely to the longitudinal direction of the cartridge 116. Through this a larger cleaning cross-section (through-flow area) can be attained. The cleaning section 121 may have a filter or a sieve. In the case of the exemplary embodiment the cleaning section 121 is formed by means of a sleeve section 122 tapered in cross-section, the wall of which has a plurality of small sieve holes 121*a* which serve for the cleaning of the flow of medium when this medium flows out of the free space 123 outside the tapered sleeve section 122 into the channel 124 running axially in the sleeve section 122. The free space 123 is preferably formed to be ring-shaped. The cross-sectional shape of the sleeve section 122 may be round. In the case of the exemplary embodiment the sleeve section 122 has a flat cross-sectional shape. Through this, the surface or wall area of the sleeve section 122 is increased, so that a greater number of the sieve holes 121*a* can be realized and thus the throttling taking place upon through-flow of the sleeve section 122 can be kept small. This is attained by means of a relatively great through-flow cross-section.

For the sealing of the at least one free space 123 the cartridge 116 has a flange 125 forwardly bounding the free space 123 which flange extends with slight play for movement up to the inner surface of the plug-in recess 117 and thereby forms a seal. Thus, the cartridge 116 consists of the flange 125, the tapered sleeve section 122 extending rearwardly therefrom, and an again thickened base section 126 to the rear, in the region of which the threaded connection section 118 and the sealing section 119 are arranged and which has on its rear side an engagement element 127 for screwing in and screwing out the cartridge. The engagement element 127 may be formed for example by means of a slot for a screwdriver.

In the case of the exemplary embodiment, the coupling element of the plug-in/turn coupling 4, here the coupling recess 7, is arranged in an insert piece 131 which is inserted from the rear into a matching plug-in recess 132 in the handpiece and fixed by means of a fixing device 133. The insert piece 131 is located in the rearward region of the handpiece 3 and ends approximately flush with its rear side. The fixing may be effected by means of a screw sleeve 134 which is screwed in from the rear between the insert piece 131 and the ring wall 135 of the handpiece 3 surrounding it, into the ring wall 135, and fixes the insert piece 131 against being pulled out rearwardly.

In particular in the rearward region the insert piece 131 has a wall thickness, here a ring wall, which is radially greater than the plug-in recess 104 or 117, so that this can be arranged therein approximately axis-parallel. In the forward region the insert piece 131 may be tapered and have a flange 136 for centering in the plug-in recess 132. Through this, there is created space for the at least one media line 11*c*, whereby in the flange 136 there is at least one through-opening 137 for the at least one media line. The screw sleeve 134 has at its rearward end a non-illustrated rotary engagement element, accessible from the rear, for a tool for screwing in and screwing out.

The cartridge 116 is preferably of plastics, whereby it is in particular an injection moulded part which despite its complicated shape can be simply and rapidly and thus economically produced by injection moulding.

The cartridge 116 is located in a user friendly position. It can be screwed out and screwed in rapidly and in a user friendly manner, e.g. exchanged for a new cartridge 116. Also a check of cleaning can be simply and rapidly carried out by means of a screwing out and screwing in of the cartridge 116. Since the cartridge 116 is accessible from the rear, it is not visible from the side of the handpiece 3 and is arranged in a protected manner. A special cover is not necessary. The appearance of the handpiece 3 is thus not adversely affected through the presence of the cartridge 116.

The invention claimed is:

1. Medical or dental-medical handpiece having a rearward end with a coupling element for coupling with a matching coupling element of a flexible supply line, and a forward region with a holder device for a tool, the handpiece comprising:

rearward and a forward handpiece sections which are connected with one another by means of a plug-in connection and are fixed on one another by means of a latching device which has a latching arm extending approximately axis-parallel and which is transversely elastically bendable, which latching arm is arranged on a plug-in connection part and is latched in its free end region with a latching element arranged on another plug-in connection part; and an insert part disposed in a recess of at least one plug-in connection part, the latching device at the same time axially fixing the insert part of the handpiece by the latching element engaging the insert part.

2. Handpiece according to claim 1, wherein the latching arm has the cross-sectional shape of a portion of an approximately cylindrical section.

3. Handpiece according to claim 1, wherein the latching arm is arranged on the rearward plug-in connection part and extends forwardly.

4. Handpiece according to claim 3, wherein the latching arm is convergent toward a center axis of the rearward and forward handpiece sections.

5. Handpiece according to claim 1, wherein the plug-in connection parts are formed by means of a sleeve attachment extending forwardly from the rearward handpiece section and a sleeve section extending rearwardly from the forward handpiece section.

6. Handpiece according to claim 5, wherein the sleeve attachment and the sleeve section are arranged next to each other and sit with slight play for movement on an insert part.

7. Handpiece according to claim 1, wherein
the latching element is formed by means of a pin or a ball, which sits in a hole of the associated plug-in connection part.

8. Handpiece according to claim 7, wherein
the pin or the ball projects inwardly beyond the sleeve attachment and engages into a recess of the insert part.

9. Handpiece according to claim 7, wherein the pin or bell sits in a hole of the forward sleeve attachment.

10. Handpiece according to claim 1, wherein there are provided, lying opposite to one another, a plurality of latching devices.

11. Handpiece according to claim 1, wherein
the insert part is a bearing sleeve through which there extends a drive shaft and which is rotatably mounted in bearings arranged at the ends in the bearing sleeve.

12. Medical or dental-medical handpiece having a rearward end with a coupling element for coupling with a matching coupling element of a flexible supply line, and a forward region with a holder device for a tool, the handpiece comprising:
rearward and a forward handpiece sections generally extending along a center axis and which are connected with one another by means of a plug-in connection and are fixed on one another by means of a latching device which has a latching arm extending approximately along the center axis and which is transversely elastically bendable, which latching arm is arranged on one plug-in connection part and is latched in its free end region with a latching element arranged on another plug-in connection part, wherein
the latching arm is arranged in the rearward plug-in connection part, extends forwardly from this plug-in connection part and with regard to its radial outer dimensions is formed or arranged to be forwardly convergent toward the center axis.

13. Handpiece according to claim 12, wherein the latching arm is externally tapered in a step-like manner.

14. Handpiece according to claim 12, wherein
the forward end region of the latching arm engages into a recess or a flattening of the plug-in connection part.

* * * * *